United States Patent [19]
Ax et al.

[11] Patent Number: 5,962,241
[45] Date of Patent: *Oct. 5, 1999

[54] MONOCLONAL ANTIBODY DETECTION OF PROTEINS ON SPERM RELATED TO FERTILITY

[75] Inventors: Roy L. Ax; Mary E. Bellin, both of Tucson, Ariz.

[73] Assignee: The University of Arizona, Tucson, Ariz.

[*] Notice: This patent is subject to a terminal disclaimer.

[21] Appl. No.: 08/487,168

[22] Filed: Jun. 7, 1995

Related U.S. Application Data

[63] Continuation-in-part of application No. 08/005,869, Jan. 15, 1993, Pat. No. 5,434,139, which is a continuation of application No. 07/386,954, Jul. 28, 1989, abandoned.

[51] Int. Cl.$^6$ .................................................. G01N 33/53
[52] U.S. Cl. .............................. 435/7.92; 435/7.1; 435/4; 530/350
[58] Field of Search ..................... 435/7.92, 7.1, 435/4; 424/143.1, 141.1, 130.1; 530/388.22, 388.1, 380, 350

[56] References Cited

U.S. PATENT DOCUMENTS 5,434,139  7/1995  Ax et al. .................................. 514/21

OTHER PUBLICATIONS

Sevier et al, Clinical Chemistry, vol. 27 (11(, pp. 1797–1806, (1981).

Koehler et al, The Journal of Cell Biology, vol. 86, pp. 529–536, (Aug. 1980).

Miller et al, Adv. Exp. Med. Biol., vol. 219, pp. 597–601, 1987.

Miller et al, Fertility and Sterility, vol. 49 (5), pp. 886–892 (May 1988).

Bellin et al, J. Anim. Sci., pp. 2441–2448, vol. 72, (1994).

Vigny et al, Eur. J. Biochem., vol. 186, pp. 733–740, (1989).

Miller et al, Adv. Exp. Med. Biol., vol. 219, pp. 597–601, (1987).

Lankes et al, Biochem. J., vol. 251, pp. 831–842, (1988).

Parrish et al, Gamete Research, vol. 24, pp. 403–413, (1989).

Patton et al, Biochem. J., vol. 311, pp. 461–469 (1995).

*Primary Examiner*—Ponnathapura Achutamurthy
*Assistant Examiner*—T. D. Wessendorf
*Attorney, Agent, or Firm*—Oblon, Spivak, McClelland, Maier & Neustadt, P.C.

[57] ABSTRACT

Heparin binding proteins (HBP) are produced by male accessory glands and bind to sperm at ejaculation. The ability of accessory glands to produce HBP and sperm to bind HBP differs among males. Identifying the presence of a 21.5, 24 and 30 kDa heparin binding proteins in sperm membranes with a monoclonal antibody resulted in separating groups of bulls by 40% difference in fertility. Thus, fertility potential of a bull can be predicted by heparin binding protein content of sperm membranes.

6 Claims, 2 Drawing Sheets

MONOCLONAL ANTIBODY DETECTION OF PROTEINS ON SPERM RELATED TO FERTILITY

This application is a continuation-in-part of U.S. Ser. No. 08/005,869, filed Jan. 15, 1993, now U.S. Pat No. 5,434,139 which is a continuation of U.S. Ser. No. 07/386,954, filed Jul. 28, 1989, now abandoned.

BACKGROUND OF THE INVENTION

1. Field of the Invention

The invention relates to novel monoclonal antibodies to heparin binding proteins and use of the same for the detection of heparin-binding proteins and for the determination of fertility.

2. Discussion of the Background

Heparin, a commercially available, sulfated glycosaminoglycan induces capacitation/acrosome reactions in sperm from bulls and rabbits (Lenz et al, Biochem. Biophys. Res. Comm., vol. 106, p. 1092, (1982); Lenz et al, Biol. Reprod., vol. 29, p. 173, (1983); Lenz et al, Biol. Reprod., vol. 28, p. 683, (1983); Lenz et al, Gamete Res., vol. 8, p. 11, (1983)). Sperm from bulls with increased fertility compared to bulls with decreased fertility have a greater frequency of acrosome reactions in response to heparin-like material (Ax et al, J. Dairy Sci., vol. 68, p. 387, (1985); Ax et al, J. Dairy Sci., vol. 70, p. 1477, (1987); Lenz et al, J. Dairy Sci., vol. 71, p. 1073, (1988)) and have a greater binding affinity for heparin (Marks et al, J. Dairy Sci., vol. 68, pp. 2078, (1985)) than sperm from less fertile bulls.

Heparin-binding proteins (HBP) are produced by the male accessory glands, secreted into seminal fluid (Nass et al, Molec. Reprod. and Devel., vol. 25, pp. 237 (1990)), and upon ejaculation bind to sperm (Miller et al, Biol. Reprod., vol. 42, pp. 899, (1990)). Addition of HBP to epididymal sperm induces heparin stimulated acrosome reactions (Miller et al, Biol. Reprod., vol. 42, pp. 899, (1990)).

Heparin-binding proteins consist of different size proteins ranging in molecular weights of 14,000 to 31,000.

Approximately five different proteins have been identified by high affinity HPLC peaks (Miller et al, Biol. Reprod., vol. 42, pp. 899, (1990); Bellin et al., J. Animal Sci., Vol. 72, pp. 2441 (1994).

However, prior to the present invention, question remained regarding which one, if any, of these HBPs were responsible for the increased fertility associated with the presence of HBP or if all or a number of HBPs were required to confer increased fertility. This information would facilitate the development of an assay which could be used to screen for fertility.

Thus, there remains a need for a method for screening for fertility. There also remains a need for reagents to be used in such a method.

SUMMARY OF THE INVENTION

Accordingly, it is one object of the present invention to provide a method for screening for fertility.

It is another object of the present invention to provide novel reagents to be used in such a method.

It is another object of the present invention to provide novel methods for the detection of heparin-binding proteins present on sperm, which are indicative of increased fertility.

It is another object of the present invention to provide novel antibodies for the detection of heparin-binding proteins present on sperm, which are indicative of increased fertility.

It is another object of the present invention to provide novel hybridomas which produce such monoclonal antibodies.

It is another object of the present invention to provide methods for isolating the various HBPs described above using monoclonal antibodies.

These and other objects, which will become apparent during the following detailed description, have been achieved by the inventors' discovery that the presence of HBPs of approximate molecular weight (MW) 30,000, 24,000 and 21,500 (HBP-30, HBP-24 and HBP-21, respectively) on sperm correlates well with increased fertility and the inventors' preparation of monoclonal antibodies which bind specifically to these HBPs.

BRIEF DESCRIPTION OF THE DRAWINGS

FIG. 2. Western blot hybridization of monoclonal antibody (MI) to sperm proteins. Each lane represents sperm from one bull. Bull samples were randomly assigned to each lane. Therefore, pictures of lanes on two blots were necessary to show all four patterns of the three proteins (30, 24 and 21.5 kDa) recognized in sperm by M1 using SIGMA FAST RED detection system. Group A had the three protein bands. Group B had a single 30 kDa band. Group C had 21.5 and 30 kDa proteins, with the 24 kDa HBP absent. Group D did not have any of the three bands present in sperm.

DETAILED DESCRIPTION OF THE PREFERRED EMBODIMENTS

Heparin Binding Proteins (HBP)

Useful HBPs in accordance with the present invention (HBPs of molecular weight (MW) of approximately 30,000, 24,000 and 21,500 (HBP-30, HBP-24 and HBP-21, respectively)) can be isolated from the semen of male animals. A particularly useful method for isolating HBPs is to purify them from seminal fluid using heparin-coupled SEPHAROSE beads (agarose beads, commercially available from Sigma Chemical Co, St. Louis Mo.) Seminal plasma is incubated with the beads, unbound protein is removed and the beads are then washed. HBPs can be eluted from the beads using a buffered solution containing salt. The HBPs can be further purified using standard procedures such as dialysis or chromatography.

Useful procedures for isolating HBPs in accordance with the present invention were described by Miller et al, Biol. Reprod., vol. 42, pp. 899 (1990).

Monoclonal Antibodies

Novel monoclonal antibodies which bind to HBP-30, HBP-24 and HBP-21 can be prepared using conventional techniques, such as that provided by Cooksley et al, MATRIX 10:285–291, 1990. Suitable antibodies are any monoclonal antibodies which specifically bind at least one of these HBPs. Typically, such antibodies will bind to the HBPs of the present invention with a $K_D$ of greater than $10^6$ mol$^{-1}$, preferably greater than $10^7$ mol$^{-1}$, more preferably greater than $10^8$ mol$^{-1}$.

Suitably, a mouse is injected with any of HBP-30, HBP-24, HBP-21 or a mixture thereof isolated from seminal fluid obtained from a vasectomized male. HBP-30 was described by Miller et al, *Biol. Reprod.*, vol. 42, pp. 899 (1990). Since HBPs are difficult to isolate in pure form, the mouse can be injected with a mixture of HBPs. To enhance the immune response and production of antibodies, the HBPs can be administered to the mouse in admixture with an adjuvant, such as Freund's Complete Adjuvant.

Typically, the HBPs are administered by injecting them interperitoneally one time every 14 days for 84 days (see Enriquez et al, *Hybridoma*, vol. 10, p. 745 (1991)). The mouse is then sacrificed, and the spleen is aseptically removed. Spleen cells are then hybridized with myeloma cells, and the resulting hybrids screened for the production of monoclonal antibodies which bind specifically to the HBPs of the present invention. Such screening may be carried out by means of ELISA and Western blotting.

Hybridoma S1A5C8G10H12 producing a monoclonal antibody referred to hereinafter as M1, and hybridoma S1A5E8C12 producing a monoclonal antibody referred to hereinafter as M2, were deposited with the American Type Culture Collection (ATCC) 12301 Parklawn Drive, Rockville, Md.) under accession Nos. HB 11915 and HB 11916, respectively, on Jun. 2, 1995. A hybridoma producing antibody S1C3 referred to hereinafter as M3 was deposited with ATCC under accession No. HB 11928 on Jun. 7, 1995.

Fertility Assay

In another embodiment, the present invention provides a method for determining fertility, by measuring the presence of HBP-30, HBP-24 and HBP-21 on the sperm of the animal being tested. In this method the presence or absence of HBP-30, HBP-24 and HBP-21 on sperm in a sample is assayed by measuring the amount, if any, of HBP-30, HBP-24 and HBP-21 on the sperm from the sample which binds to the monoclonal antibody of the present invention. The presence of the HBPs of the present invention on sperm was critical, not the amount of the HBPs.

In these assaying methods, it is essential that the sample be frozen immediately upon collection to prevent degradation of the HBPs. It is preferable to remove proteins from sperm before assaying. The proteins can be removed by solubilization with detergents or by mechanical means such as a cell disruption bomb. The collected sample can be isolated as described by Nass et al (1990) into seminal fluid and sperm pellets.

Typically, there is about $1 \times 10^9$ sperm/mL of ejaculate. However, using the methods of the present invention, it is possible to detect HBPs in a sample containing as little as 500,000 sperm.

The fertility of the bull can then be determined by screening the collected sample for the presence of the HBPs of the present invention. When all three of HBP-30, HBP-24 and HBP-21 are present on the sperm of these test bulls, 80% of cows palpated after pasturing with these bull were pregnant. In contrast, when these three HBPs were absent on the sperm of these test bulls, only 40% of cows palpated after pasturing with these bulls were pregnant. In a small percentage (2%) of the tested bulls, only HBP-30 was present on their sperm. This group of bulls had the highest degree of fertility (>85%).

A. Enzyme Linked Immunosorbent Assay (ELISA)

A preferred immunologic means of detecting HBPs is the ELISA method. ELISA plates can be purchased commercially (for example, from Falcon, Fischer Scientific, Pittsburgh, Pa.). A sample is then contacted with these plates. The samples are preferably prepared by diluting protein removed from sperm as described above in an incubation-suitable buffer. The samples are placed in the well, incubated at a temperature ranging from about 25° C. to about 37° C., and preferably at about 37° C. for a time period of from about 1 hour to about 4 hours and preferably about one hour. The wells containing the sample are washed thoroughly before introducing a detection antibody into the well such as a labeled anti-HBP antibodies.

An antibody can be directly labelled or detected using a second antibody. The label may suitably be any which is conventionally attached to monoclonal antibodies for use in an immunoassay, such as an enzyme (e.g., horseradish peroxidase), a chromophore, a fluorophore, or a radiolabel. The label may be bonded to the monoclonal antibody by any conventional method including via conventional crosslinking agents.

B. Western Blot

If Western blots or immunoprecipitation are used for testing, the sperm can be used without the need to first remove the protein.

For Western blots a typical procedure includes: 200 μL of semen is added to a 1.5 mL mico centrifuge tube with 1 mL phosphate buffered saline containing TWEEN and 1% BSA and protease inhibitors and centrifuged at 4000 rpm to remove seminal fluid. The sperm can be washed 2–3 times before adding sample buffer and boiling for 5 min prior to being applied to either 10–15%, preferably 12%, PAGE and Western blots.

For immunoprecipitation a typical procedure includes: monoclonal antibody is conjugated to HZ Beads (Sigma Chemical Co., St. Louis, Mo.). The membranes of washed sperm are lysed with detergent or with mechanical means and then removed by centrifugation. Antibody beads are added to the supernatant and protein is allowed to bind (~10 min). The beads are then washed three times, boiled in sample buffer and the sample buffer is applied to 10–15%, preferably 12%, PAGE. The presence of protein can be determined directly using any suitable protein assaying technique such as Commassie blue staining of the gels, ELISA or by Western blot.

In another embodiment, the present invention provides a method for detecting the presence of the HBPs of the present invention, by measuring the amount of the HBPs of the present invention in a sample, if any, which binds to the present monoclonal antibody which specifically binds to the HBPs of the present invention. The present assay for the HBPs of the present invention may be any conventional immunoassay which relies upon the binding of HBP-30 to the present monoclonal antibody. Thus, the present assay may be a sandwich assay, a displacement assay, a competitive assay, etc. Such assays are described in "Guide to Protein Purification", *Methods in Enzymology*, vol. 182, edited by M. P. Deutscer, Academic Press, Inc., Harcourt, Brace, Jovanovich, Publishers: San Diego, Calif., 1990 and in "Antibodies: A Laboratory Manual", by E. Harlow, Cold Spring Harbor Laboratory and D. Lane, Imperial Cancer Research Fund Laboratories, 1988; which are incorporated herein by reference.

The presence of non-bovine HBPs corresponding to the HBPs of the present invention can also be detected using the monoclonal antibodies of the present invention as they cross-react with HBPs from other species including human and other mammals, preferably, sheep, horses, porcine, dog, feline and human.

In another embodiment, the present invention provides methods for purifying the HBPs of the present invention by contacting a biological sample such as semen or ovarian tissue with an antibody according to the present invention which selectively binds said HBPs.

Other features of the invention will become apparent in the course of the following descriptions of exemplary embodiments which are given for illustration of the invention and are not intended to be limiting thereof.

EXAMPLES

Example I

Studies were performed to determine the relationship of heparin-binding proteins (HBP) to fertility of bulls. Red Angus (142), Santa Gertrudis (59), Gelbvieh (59), and Santa Gertrudis X Gelbvieh (40) bulls were identified according to the presence of absence of the greatest affinity HBP (HBP-B5) on sperm membranes and in seminal fluid. Nine to 20 bulls with the same HBP-B5 profiles were assigned to pastures with Santa Gertrudis cows at a ratio of 1 bull: 25 cows. Fertility for Group 1 (80 bulls with HBP-B5 in sperm membranes but undetectable HBP-B5 in seminal fluid, in six pastures) was 82% pregnant of 1,692 cows. Group 2 (48 bulls with HBP-B5 detectable in seminal fluid and in sperm membranes, in four pastures) impregnated 67% of 919 cows. Fertility of Group 3 (37 bulls with HBP-B5 in seminal fluid but undetectable HBP-B5 in the sperm membranes, in three pastures), and Group 4 (56 bulls with undetectable HBP-B5 in seminal fluid and sperm, in four pastures) was 63% pregnant of 747 and 1,208 cows, respectively. Group 1 had an average of 17% greater fertility compared with Groups 2, 3, and 4 (P<0.05). In conclusion, groups with the greatest affinity HBP-B5 in sperm membranes but not in seminal fluid had greater fertility than did groups with other HBP-B5 profiles.

Semen Collection

Semen samples were collected from 76 Red Angus bulls for Trial 1 and 66 Red Angus, 59 Gelbvieh, 59 Santa Gertrudis and 40 Gelbvieh X Santa Gertrudis bulls for Trial 2 using a programmable electroejaculator (Electrojac, Chicago, Ill.) at a commercial ranch (King Ranch, Kingsville, Tex.) during routine breeding soundness exams (BSE, Chenoweth et al, Society for Theriogenology, Proc: for Annu. Mtq, August 14–15, San Antonio, Tex., (1992)) before spring breeding. Trials were conducted during two consecutive years. Bulls were 2 to 7 years of age. Sperm samples were examined visually for motility using a phase contrast microscope. One hundred sperm from an ejaculate were examined and visually identified as having normal or abnormal structure using a morphology stain (Society for Theriogenology, Hastings, Nebr.) and a light microscope (1000× magnification). Sperm were further characterized as having primary (head) or secondary (tail) abnormalities. In addition, scrotal circumference for each bull was measured. Semen (1 mL) was diluted with 0.8 mL TC buffer (40 mM Tris(hydroxymethyl)aminomethane, 2 MM $CaCl_2$, 0.01% sodium azide, 1 mm pepstatin A, 1 mM phenylmethylsulfonyl fluoride, Sigma Chemical Co., St Louis, Mo., pH 7.4). Diluted semen samples were frozen, shipped with dry ice to the University of Arizona (Tucson, Ariz.) and stored at –70° C. until they were analyzed for HBP. Collection and freezing of semen samples occurred as quickly as possible and simultaneously with BSE evaluation. Bulls with less than 70% normal sperm were removed from study and not used for breeding, but semen samples from these failed bulls were collected and later identified and used for laboratory analysis.

Protein Purification

Seminal Fluid Protein. Proteins were isolated from seminal fluid (Nass et al, 1990). Thawed semen was diluted to a final volume of 2.5 mL in TC buffer and centrifuged at 1,200× g for 15 min at 4° C. Supernatant was carefully removed without disturbing the sperm pellet, applied to a PD-10 SEPHADEX G-25M column (BioRad, Hercules, Calif.) and washed with 0.05 M ammonium bicarbonate (pH 8.5) to remove excess salt. The sample was lyophilized and stored at –20° C. until it was analyzed for HBP. The sperm pellets were frozen (–70° C.) until they were isolated for proteins.

Sperm Membrane Proteins. Sperm pellets were thawed and washed three times with 1 mL of TC buffer at 4° C. To determine the number of sperm, 50 µL were pipetted and diluted to 250 µL and 10 µL were counted using a hemacytometer. washed pellets were resuspended in 1 mL of TC buffer with 0.1% TRITON X-100 and incubated for 1 h at 4° C., then 3 mL of 0.1% TC buffer was added and the cells were centrifuged at 50,000× g for 30 min to pellet cellular debris. Supernatants containing sperm membrane proteins were lyophilized and stored at –20° C. until they were analyzed for HBP (Nass et al, 1990).

Heparin Affinity High-Performance Liquid Chromatography.

Seminal fluid and sperm membrane proteins were solubilized in 500 and 200 µL of deionized distilled water, respectively. Seminal fluid or sperm membrane proteins were applied (100 µL) to a HPLC (Hitachi, San Jose, Calif.) heparin affinity column (Pierce Chemical Company, Rockford, Ill., Miller et al, 1990). Protein peaks were detected with a Hitachi D6000 detector at $A_{280}$ nm. Unbound proteins were removed with 25 mL of TC buffer (1.0 mL/min), and bound HBP were eluted with a 60 min linear gradient of 0 to 1.5 M NaCl. Five protein peaks bound (B) to heparin and eluted as the NaCl concentrations were increased from 0.1 to 1.2 M. The HBP peaks were labeled B1 to B5 with HBP-B1 corresponding to the peak with the least affinity for heparin and HBP-B5 corresponding to the peak with the greatest affinity for heparin (Table 1). Heparin-binding protein concentrations were determined by comparing HBP peak areas to known concentrations of protein standards (BioRad, Hercules, Calif.).

TABLE 1

Molarity and elution times of the five heparin-binding proteins (HBP) bound (B) to a heparin affinity HPLC column

| HBP | Elution time, Min | | Molarity |
|---|---|---|---|
| Peak | Range | Mean | (NaCl) |
| B1 | 36–39 | 38.4 | 0.4 |
| B2 | 45–48 | 45.9 | 0.63 |
| B3 | 51–55 | 52.9 | 0.84 |
| B4 | 56–58 | 57.1 | 0.96 |
| B5 | 61–65 | 64.9 | 1.19 |

Experimental Design

Grouping of Bulls According to Heparin-Binding Protein Profiles.

Trials were conducted at a large commercial ranch (King Ranch, Kingsville, Tex.), and it was not possible to test fertility of individual bulls. Instead, bulls were identified and grouped according to the presence or absence of HBP-B5 in sperm membranes and seminal fluid. Group 1 was comprised of bulls with HBP-B5 on sperm but with undetectable HBP-B5 in fluid. Group 2 had bulls with HBP-B5 detectable on sperm and in fluid. Bulls with HBP-B5 in fluid but not in sperm were in Group 3 and bulls with undetectable HBP-B5 in fluid and sperm were in Group 4.

Pasture Assignments. Groups were assigned to a pasture based on the number of bulls need to meet the pasture requirements. Bulls were pastured at a ratio of 1 bull:25 cows, resulting in nine to 20 bulls of the same breed from one HBP-B5 group in a pasture. If a group contained large numbers of bulls, bulls were divided and assigned to two pastures. To eliminate bias of selection of pastures, actual HBP-B5 group numbers were coded and not identified to King Ranch personnel until completion of the trials. Pastures contained native grasses, and cattle were supplemented with MINTRATE mineral blocks (MoorMan's Mfg. Co., Quincy, Ill.).

Identifying Bulls: Bulls were identified by ear tags, matched to their coded HBP-B5 group and the appropriate pasture assignment was spray painted on their back. Bulls were transported to each pasture. In Trial 2, some bulls were lost during the period from BSE to sorting or unidentifiable, so bulls that had passed the BSE, but did not have HBP-B5 determined, were used to meet the required numbers needed for the pastures.

Santa Gertrudis Cows: All cows used in these studies were Santa Gertrudis and had calved in the spring before the trial: however, young cows in their second breeding season were used in Trial 1, whereas, older cows that had at least two previous calvings were used in Trial 2.

Determination of Fertility. Bulls were pastured on approximately May 1 with cows for 60 d, then they were removed. After an additional 60 d, cows were checked for pregnancy by palpation per rectum. Because the pastures were large, not all cows were recovered from each pasture at the time of palpation. Fertility for each group of bulls was computed as the number of cows determined pregnant divided by the total number of cows palpated.

Statistics

Statistical significance of the differences in fertility (the proportion of pregnant Cows palpated for each HBP-B5 group) were determined by comparing two HBP-B5 groups within a breed by Z-test. Since large numbers of cows were compared, the distributions of the proportions could be assumed to be approximately normal and therefore the Z-test was used (Geng et al, in *Biometrics in Agricultural Science*, Kendall Hunt, ed., p. 67 (1992)). Concentrations of individual HBP (B1 to B5) and total HBP (B1 to B5 added together) in seminal fluid and sperm membrane were determined for each Red Angus bull in Trial 1. The HBP values were transformed using the formula, $\log (x+1)$ before statistical analyses were performed. Physical BSE characteristics (scrotal circumference, motile sperm (%), normal and abnormal sperm, %) were determined for each Red Angus bull in Trial 1. Concentration of sperm per milliliter of seminal fluid was determined for each bull in Trial 2. To determine if selection of bulls resulted in differences in HBP concentrations or physical characteristics, each measurement was compared among HBP-B5 groups with one-way classification ANOVA. Significant differences among class means were determined with Fisher paired LSD (STATVIEW 512+, BrainPower, Calabasas, Calif.). Concentrations of sperm were also compared among the breeds of bulls with ANOVA and Fisher paired LSD.

Results

Relationship Of Numbers of Bulls Among Heparin-Binding Protein Groups

A total of 300 bulls was tested for presence or absence of the greatest affinity HBP (HBP-B5, Table 1) in sperm membranes and seminal fluid (Table 2). Differences in the number of bulls among HBP-B5 groups were observed for each breed (Table 2). Red Angus (36 and 38%, for Trials 1 and 2, respectively) and Santa Gertrudis (42%) had a greater percentage of bulls in Group 1 (bulls with detectable HBP-B5 in sperm but undetectable HBP-B5 in membranes) than other groups. Gelbvieh had more bulls in Group 2 (56%, with HBP-B5 in sperm and fluid) and Gelbvieh x Santa Gertrudis had a greater percentage of the bulls in Group 4 (50%, with undetectable HBP-B5 in sperm and fluid) compared with other groups. Determinations of HBP-B5 on sperm membrane samples from 17 Santa Gertrudis and 5 Gelbvieh x Santa Gertrudis bulls were not completed by the time bulls were sent to pasture, therefore it could not be determined if these bulls belonged in Group 2 or Group 3 (bulls with HBP-B5 in fluid but undetectable in sperm).

TABLE 2

Number of bulls tested and percent (%) of bulls from each breed among the HBP-B5 groups

| | Sperm with HBP-B5 | | Sperm without HBP-B5 | |
| --- | --- | --- | --- | --- |
| Bull breed | HBP-B not in fluid Group 1 | HBP-B5 in fluid Group 2 | HBP-B5 in fluid Group 3 | HBP-B5 not in fluid Group 4 |
| Red Angus Trial 1 | 27(36) | 13(17) | 18(23) | 18(24) |
| Red Angus Trial 2 | 25(38) | 10(15) | 14(21) | 17(26) |
| Gelbvieh | 10(17) | 33(56) | 12(20) | 4(7) |
| Santa Gertrudis | 25(42) | a | a | 17(29) |
| Gelbvieh x Santa Gertrudis | 15(37) | b | b | 20(50) |
| Summary | 102(37) | 56(20) | 44(16) | 76(27) | ab Determination of HBP-B5 on the sperm membranes for 17 Santa Gertrudis and 5 Gelbvieh x Santa Gertrudis bulls was not completed at time bulls were pastured.

Pasture Assignments

Not all bulls that were tested for HBP-B5 were assigned to pastures (Table 3). Bull assignments resulted in 58 Red Angus bulls bred to 1,302 cows in five pastures on 10,747 ha for Trial 1. Group 1 Red Angus bulls were divided into two pastures. Trial 2 had 58 Red Angus, 40 Gelbvieh, 34 Santa Gertrudis and 32 Gelbvieh x Santa Gertrudis bulls bred to a total of 4,024 cows in 12 pastures on 25,061 ha (Table 3). There were enough Gelbvieh, Group 2 and Santa Gertrudis, Group 1 bulls to assign to two pastures. Trial 2, Red Angus groups had bulls that were not tested for HBP-B5 (Group 1; 2 of 20, Group 2; 2 of 9, Group 3; 7 of 15 and Group 4; 5 of 14). Three other pastures differed from the 17 pastures used in these studies. One contained 11 of the 17 Santa Gertrudis bulls that did not have HBP-B5 measured in the sperm membrane but had HBP-B5 present in seminal fluid (Group 2 or 3), pastured with 279 cows on 1,672 ha. The second had five Gelbvieh x Santa Gertrudis bulls, that belonged in Group 2 or 3 and five Gelbvieh x Santa Gertrudis bulls that had not been tested for HBP-B5, but had passed the BSE, pastured with 249 cows on 1,907 ha. The third had Gelbvieh bulls (Group 1) with 294 Santa Gertrudis cows that had not produced a calf the previous two breeding seasons. Because these three pastures differed, data were recorded but not used for final analyses.

TABLE 3

Pasture assignments including number of bulls from each breed,
number of Santa Gertrudis cows and pasture size (ha) for each HBP-B5 group.

|  | Sperm with HBP-B5 | | | | Sperm without HBP-B5 | |
| --- | --- | --- | --- | --- | --- | --- |
|  | HBP-B5 not in fluid Group 1 | | HBP-B5 in fluid Group 2 | | HBP-B5 in fluid Group 3 | HBP-B5 not in fluid Group 4 |
| Pastures | 1 | 2 | 1 | 2 | 1 | 1 |
| Trial 1: | | | | | | |
| Red Angus bulls, n | 11 | 12 | 9 | | 13 | 13 |
| Cows, n | 230 | 255 | 233 | | 294 | 290 |
| Pasture, ha | 1,754 | 2,591 | 964 | | 2,803 | 2,635 |
| Trial 2: | | | | | | |
| Red Angus bulls, n | 20[a] | 9[a] | | | 15[b] | 14[c] |
| Cows, n | 494 | 220 | | | 379 | 289 |
| Pasture, ha | 1,754 | 635 | | | 3,017 | 878 |
| Gelbvieh bulls, n | 13 | 14 | 16 | | 9 | |
| Cows, n | 294[d] | 349 | 429 | | 218 | |
| Pasture, ha | 2,803 | 1,754 | 3,730 | | 2,509 | |
| Santa Gertrudis bulls | 11 | 9 | [e] | | [e] | 14 |
| Cows, n | 260 | 225 | | | | 354 |
| Pasture, ha | 2,362 | 1,370 | | | | 2,269 |
| Gelbvieh × Santa Gertrudis bulls, n | 17 | | [f] | | [f] | 15 |
| Cows, n | 426 | | | | | 380 |
| Pasture, ha | 2,591 | | | | | 963 |
| Total bulls, n | 80 | | 49 | | 37 | 56 |
| Total cows, n | 1,891 | | 1,231 | | 891 | 1,313 |
| Total pasture, ha | 12,423 | | 8,309 | | 8,329 | 6,746 |

[a]includes two bulls not tested for HBP-B5.
[b]includes seven bulls not tested for HBP-B5.
[c]includes five bulls not tested for HBP-B5.
[d]cows did not produce a calf the previous two breeding seasons.
[e]11 Santa Gertrudis bulls not tested for HBP-B5 in the sperm membranes but had HBP-B5 in fluid were pastured with 279 cows on 1,672 ha.
[f]five Gelbvieh × Santa Gertrudis bulls not tested for HBP-B5 in the sperm membranes but had HBP-B5 in fluid, and five untested bulls were pastured with 249 cows on 1,907 ha.

Relationship of Fertility Among Groups

Group 1 was more fertile compared with the other groups (P<0.05, Table 4). Fertility for Group 1 (HBP-B5 in sperm membranes but undetectable HBP-B5 in seminal fluid) was 82% of 1,692 cows. Group 2 (HBP-B5 detectable in seminal fluid as well as in sperm membranes) had 67% pregnant of 919 cows. Group 3 (detectable HBP-B5 in the seminal fluid and undetectable HBP-B5 in the sperm membranes) and Group 4 (undetectable HBP-B5 in the seminal fluid and sperm membrane) had 63% of 747 and 1,208 cows pregnant, respectively.

Comparisons among groups of Red Angus bulls in Trial 2 indicated Group 1 had greater fertility than the other groups even when nearly 50% of the bulls were not tested for HBP-B5. The three pastures that were different from the other 17 used in these studies indicated that fertility for Gelbvieh x Santa Gertrudis bulls, where 50% of the bulls were Group 2 or 3, and 50% were not tested, was 81% and not different from Group 1 (80%). In the case of the Santa Gertrudis bulls where determination of Group 2 or 3 could not be made, fertility was 77%, less than Group 1 (89 and 92%) and in the same range of fertility of other breeds of bulls in Groups 2 and 3. Interestingly, fertility was 50% for cows that had not produced a calf the previous two breeding seasons when bred to Group 1 bulls.

Fertility ranged from 40 to 92% cows pregnant per pasture (Table 4). Because of the number of bulls needed to fill each pasture, it was difficult to have two pastures of each group of bulls within a breed. But, in the few examples available, fertility among pastures was 70 and 74% for Trial 1—Red Angus bulls in Group 1; 89 and 92% for Santa Gertrudis bulls in Group 1; 72 and 75% for Gelbvieh bulls in Group 2 (Table 4).

Average fertility (Groups 1 to 4) for all breeds of bulls was calculated to be 71% (Table 5). Santa Gertrudis bulls had the greatest average fertility of 85%. Red Angus bulls had the least average fertility of 58% during Trial 1 and 75% during Trial 2. Average fertility among Red Angus bulls in Trials 1 and 2 differed by 17%; this could have been due to use of young cows in Trial 1 and older cows in Trial 2, or environmental conditions which were classified as drought-like during the first trial and above average rainfall during the second trial. Regardless of environmental conditions or type of cow used, differences among Group 1 and average fertility were similar for each trial (14% for Trial 1 and 10% for Trial 2) and was 11% for all breeds (Table 5). Differences among Group 1 and less fertile groups (Groups 2, 3 and 4) for Red Angus bulls were also similar among trials (22% for Trial 1 and 18% for Trial 2, Table 5) and was 17% for all breeds (Table 5).

TABLE 4

Fertility (number of pregnant cows divided by total number of cows palpated, %)
for each breed of bull within a pasture and among HBP-B5 groups

| | HBP-B5 is sperm | | | | HBP-B5 not in sperm | |
| --- | --- | --- | --- | --- | --- | --- |
| | HBP-B5 not in fluid Group 1 | | HBP-B5 in fluid Group 2 | | HBP-B5 in fluid Group 3 | HBP-B5 not in fluid Group 4 |
| Pastures | 1 | 2 | 1 | 2 | 1 | 1 |
| Trial 1; Red Angus bulls | | | | | | |
| Fertility, % | 70[a] | 74[a] | 57[b] | | 40[c] | 56[bc] |
| Cows palpated, n | 230 | 255 | 233 | | 294 | 290 |
| Trial 2; Red Angus bulls | | | | | | |
| Fertility, % | 85[a] | | 62[bc] | | 74[b] | 63[c] |
| Cows palpated, n | 497 | | 157 | | 262 | 274 |
| Gelbvieh bulls | | | | | | |
| Fertility, % | d | | 72[b] | 75[b] | 84[b] | |
| Cows palpated, n | | | 247 | 282 | 191 | |
| Santa Gertrudis bulls | | | | | | |
| Fertility, % | 89[a] | 92[a] | e | | e | 84[a] |
| Cows palpated, n | 179 | 175 | | | | 272 |
| Gelbvieh × Santa Gertrudis bulls | | | | | | |
| Fertility, % | 80[a] | | f | | f | 54[b] |
| Cows palpated, n | 356 | | | | | 963 |
| Summary | | | | | | |
| Fertility, % | 82[a] | | 67[b] | | 63[b] | 63[b] |
| Total palpated, n | 1,692 | | 919 | | 747 | 1,208 |

[a,b,c] Value with different superscripts differ (p. < 0.05)
[d] fertility was 50% of 154 palpated cows. Because the cows had not produced a calf the previous two breeding seasons, data were not used in final calculations.
[e] fertility was 77% of 245 palpated cows bred to 11 Santa Gertrudis bulls not tested for HBP-B5 in the sperm membranes but had HBP-B5 in fluid. It was not possible to determine if bulls belonged in Group 2 or 3 and data were not used in final calculations.
[f] fertility was 81% of 181 palpated cows bred to five Gelbvieh × Santa Gertrudis bulls not tested for HBP-B5 in the sperm membranes but had HBP-B5 in fluid, and five untested bulls. It was not possible to determine what group the bulls belonged in and data were not used in final calculations.

TABLE 5

Calculated fertility for all pastures in Group 1 (average of greatest fertility bulls), Groups 1 to 4 (average of all groups in study), and Groups 2 to 4 (average of least fertile groups) for each breed

| | Average Fertility for | | | Difference between Group 1 and | |
| --- | --- | --- | --- | --- | --- |
| Bull breed | Group 1 | Groups 1 to 4 | Groups 2 to 4 | Groups 1 to 4 | Groups 2 to 4 |
| Red Angus Trial 1 | 72 | 58 | 50 | 14 | 22 |
| Red Angus Trial 2 | 85 | 75 | 67 | 10 | 18 |
| Gelbvieh | — | 76 | 76 | — | — |
| Santa Gertrudis | 90 | 85 | 81 | 5 | 9 |
| Gelbvieh × Santa Gertrudis | 80 | 67 | 54 | 13 | 26 |
| Summary | 82 | 71 | 65 | 11 | 17 |

Relationship Of Heparin Binding Protein Among Groups

To determine if grouping of bulls based on presence or absence of HBP-B5 resulted in differences of HBP, concentrations of HBP-B1 to B5 were calculated and compared among the HBP-B5 groups for Trial 1 (Table 6). Total HBP (B1 to B5 added together) concentrations in the fluid averaged 19.2 mg/mL of ejaculate and were not different among assigned HBP-B5 groups (p>0.05). Sperm membranes contained less than 1% of the total amount of HBP found in fluid (0.14 mg/mL of ejaculate in sperm membranes), but concentrations of total HBP in sperm membranes did not differ among HBP-B5 groups (p>0.05).

HBP-B5 concentrations varied from 0 to 39% of total HBP concentrations among the four groups (Table 6). HBP-B5 comprised 30% (44.2 of 177 $\mu$g/mL) of the total HBP in sperm membranes but HBP-B5 was undetectable in seminal fluid for Group 1. Group 2 had 17% (17.1 of 120 $\mu$g/mL) of the total sperm membrane HBP and 32% (3.7 of 11.4 mg/mL of ejaculate) of the total seminal fluid HBP as HBP-B5. Group 3 had undetectable amounts of HBP-B5 in sperm membranes but HBP-B5 was 39% (6.5 of 16.4 mg/mL of ejaculate) of the total HBP in seminal fluid. Group 4 had undetectable HBP-B5 in sperm membranes and seminal fluid. Results from Trial 1 indicated concentrations of total HBP did not differ but concentrations of HBP-B5 did differ among groups.

TABLE 6

Concentrations of total heparin-binding proteins (HBP) and the greatest affinity HBP (HBP-B5) in seminal fluid (mg) and sperm membranes (μg) from 1 mL of ejaculate from Red Angus bulls (Trial 1) among the HBP-B5 groups (average ± SEM)

|  | Sperm with HBP-B5 | | Sperm without HBP-B5 | |
| --- | --- | --- | --- | --- |
|  | HBP-B5 not in fluid Group 1 | HBP-B5 in fluid Group 2 | HBP-B5 in fluid Group 3 | HBP-B5 not in fluid Group 4 |
| Total HBP in fluid, mg/mL | 25.8 ± 6.1[a] | 11.4 ± 2.4[a] | 16.8 ± 4[a] | 23.1 ± 2.3a |
| HBP-B5 in fluid, mg/mL | 0[a] | 3.7 ± 1.3[b] | 6.5 ± 1.5[c] | 0[a] |
| Total HBP in sperm, μg/mL | 147 ± 39[a] | 120 ± 33[a] | 128 ± 33[a] | 184 ± 50[a] |
| HBP-B5 in sperm, μg/mL | 44 ± 17[b] | 17 ± 7[ab] | 0[a] | 0[a] |

[a,b,c]Values in the same row with different superscripts differ ($p < 0.05$).

Relationship Of Physical Characteristics Of Sperm Among Groups

All bulls used in these fertility studies had met or exceeded BSE requirements. To determine if grouping of bulls by presence or absence of HBP-B5 resulted in groups with different physical characteristics: scrotal circumference, sperm motility, and percent structurally abnormal sperm were compared (Trial 1) and indicated no differences among HBP-B5 groups (Table 7).

Estimated concentrations of sperm/mL of ejaculate were calculated for bulls in Trial 2 (Table 7). Sperm numbers were not different among HBP-B5 groups ($p>0.05$) but were different among breeds of bulls ($p<0.001$). Concentrations of sperm were $2.0 \times 10^9$/mL of ejaculate for Gelbvieh x Santa Gertrudis crosses, $1.4 \times 10^9$/mL for Santa Gertrudis, $1.1 \times 10^9$/mL for Red Angus and $0.9 \times 10^9$/mL for Gelbvieh bulls. Thus, presence or absence of HBP-B5 on sperm membranes were not related to the total number of sperm in an ejaculate.

Samples from bulls (n=38) that failed the BSE and were not used in these studies, were available for determination of HBP-B5 profiles in Trial 2. Failed bulls (10, 7, 2 and 7) would have been identified in each HBP-B5 profile (Group 1, 2, 3 and 4, respectively). An additional 12 failed bulls would have been identified as either Group 2 or 3, but the HBP-B5 content of the sperm membranes was not determined.

TABLE 7

Average breeding soundness exam (BSE) values for Red Angus bulls (Trial 1) and average total sperm number in 1 mL of ejaculate for bulls in Trial 2 (average ± SEM)[a] among the HBP-B5 groups

|  | Sperm with HBP-B5 | | Sperm without HBP-B5 | |
| --- | --- | --- | --- | --- |
| BSE variable | HBP-B5 not in fluid Group 1 | HBP-B5 in fluid Group 2 | HBP-B5 in fluid Group 3 | HBP-B5 not in fluid Group 4 |
| Scrotal, cm | 38 ± 3 | 39 ± 4 | 39 ± 4 | 39 ± 4 |
| Motility, % | 54 ± 8 | 60 ± 9 | 56 ± 6 | 59 ± 7 |
| Normal sperm, % | 84 ± 7 | 83 ± 7 | 83 ± 6 | 83 ± 8 |
| Abnormal sperm: | | | | |
| Primary, % | 12 ± 4 | 11 ± 6 | 12 ± 4 | 13 ± 6 |
| Secondary, % | 5 ± 5 | 5 ± 5 | 4 ± 3 | 4 ± 3 |
| Total sperm, $10^9$ | 1.4 ± .1 | 1.0 ± .1 | .7 ± .2 | 1.7 ± .2 |

[a]Values within a variable did not differ significantly ($p > 0.05$).

In conclusion, these studies indicated that identifying bulls with the greatest affinity heparin-binding (HBP-B5) on the sperm membranes but absent in the seminal fluid resulted in 17 percentage points greater fertility compared with bulls with other HBP-B5 profiles.

Example II

Screening With Monoclonal Antibody:

A monoclonal antibody (M1) was produced against seminal fluid heparin-binding proteins (HBP) from a vasectomized bull. In the first part of this study, presence of HBP in sperm or seminal fluid was determined for 53 bulls with an enzyme linked immunosorbent assay (ELISA) using M1. Bulls (8 to 18 per pasture) were bred to 1,114 crows at ratios of 1 bull:25 cows. Bulls with detectable HBP on sperm membranes were 11 percentage points more fertile than bulls with undetectable HBP in sperm membranes. In the second part of this study, three sperm membrane proteins approximately 30, 24, and 21.5 kDa were identified using Western blots. Santa Gertrudis bulls (n=64) were bred to 1,354 Santa Gertrudis cows in groups of 2 to 11 bulls. Bulls with those three HBP (Group A) or a single 30 kDa HBP (Group B) in sperm membranes had the greatest fertility, ranging from 74.4 to 89.9% with an average of 81.5% of the palpated cows pregnant. Bulls with 21.5 and 30 kDa HBP, and the 24 kDa HBP was absent (Groups C) had reduced fertility of 61.3%. Bulls without detectable HBP (Group D) resulted in 41.9% of 186 cows palpated pregnant. Bulls in Groups A and B were more fertile than all other groups. In conclusion, presence of HBP in sperm membranes was indicative of fertility potential of a bull.

Production Of Monoclonal Antibody

Coupling Heparin To Sepharose Beads. Heparin (sodium salt from porcine intestinal mucosa, Scientific Proteins Lab, Waunakee, Wis.) was coupled to cyanogen bromide-activated SEPHAROSE 4B (Pharmacia, Piscataway, N.J.). SEPHAROSE (3 g) and heparin (300 mg) were incubated at room temperature for 2 h and then washed by centrifugation (2000× g) with 40 mM T TRIZA® base pH 7.4; Sigma Chemical, St Louis, Mo.). Then the beads were equilibrated in 40 mM T with 2 mM $CaCl_2$, 0.05% sodium azide, 1 mM phenylmethylsulfonylfluoride, and 1 μM pepstatin A (TC, Sigma Chemical).

Isolation Of Heparin-Binding Proteins. Heparin binding proteins were initially purified using heparin-coupled SEPHAROSE beads. Commercially prepared heparin-coupled agarose beads (Sigma Chemical) were also used to prepare heparin-binding proteins. Briefly, seminal plasma (10 mL) from a vasectomized Holstein bull (provided by 21st Century Genetics, Shawano, Wis.) was added to approximately 1 g of heparin-coupled beads and gently mixed for 10 min. Unbound protein was removed by centrifuging beads (2,000× g) for 10 min with 50 mL of TC buffer; and three additional washes with 10 mL of TC buffer were performed. Proteins bound to heparin SEPHAROSE beads (heparin-binding proteins, HBP) were eluted from beads with 20 mL of TC buffer containing 2 M NaCl. Salt was removed from HBP by dialysis in SPECTRA/POR molecular porous membrane tubing with a 10,000 molecular weight cut off (Spectrum Medical Industries, Houston, Tex.) in 1 L of 50 mM ammonium carbonate buffer (Sigma Chemical) for 18 h at 4° C., and buffer was changed at least four times. Dialyzed HBP was lyophilized and stored as a powder. The yield was approximately 7 mg of HBP/mL of seminal fluid.

In Vivo Immunization Of Mice With Heparin-Binding Proteins. Monoclonal antibodies to HBP were generated at the Hybridoma Technology Core Support Facility at the University of Arizona according to the procedures of Enriquez et al (1991). Three female (8 to 12 wk old) Balb/cByJ mice (Jackson Laboratories, Bar Harbor, Me.) were immunized intraperitoneally six times at 14-d intervals with approximately 60 μg of purified HBP antigen mixed in Freund's complete adjuvant for the first injection and Freund's incomplete adjuvant for the following injections in 200 μL volume. Mice were sedated with carbon dioxide and bled from the retroorbital plexus. Serum was tested for the presence of antibodies to HBP using an ELISA and specifically to individual HBP using Western blot analysis (described later). The mouse with the highest antibody titer to the HBP was selected for the fusion. Serum was stored at −80° C. and used as the positive control during screening of hybrids. Three days after the final immunization, the selected mouse was killed by cervical dislocation and the spleen was aseptically removed. Spleenocytes were dispersed into a single cell suspension.

Hybridization Of Cells. Spleen cells ($1 \times 10^8$) and SP2/0 myeloma cells ($1 \times 10^7$) in RMPI-1640 complete media were fused with polyethylene glycol (4,000 mw, EM Science, Gibbstown, N.J., Kohler and Milstein, 1975). Hybridized cells were diluted to 100 mL, pipeted into 24 well culture plates at approximately $1 \times 10^5$ cells/mL and cultured for 10 to 14 d before supernatants were assayed for antibody production with ELISA and Western blots. Cells identified as producing antibody to the 30 kDa HBP were further cloned or frozen in 10% DMSO and stored in liquid nitrogen.

Cloning Of Cells. Positive hybrids were cloned three times by limiting dilution. Briefly, a selected positive hybrid (50 μL of $1 \times 10^4$ cells/mL) was diluted to 5 mL, then 100 ML were pipetted into each well of the first two rows (Rows A and B with 12 wells/row) of a 96 well plate (10 cells/well). An additional 2.5 mL of fresh media were added to the cells, then 100 μL were pipetted into the third and fourth row (Rows C and D, 5 cells/ well). This procedure was repeated until the 96 well plate was completed with 1 cell/well in rows G and H. Cells received RPMI media with 10% BSA on d 5 and 10 and were monitored for antibody production on d 10 with ELISA and Western blots.

Development Of Monoclonal Antibody. One monoclonal antibody (S1A5C8G1OH12, referred to as M1) recognized the 30 kDa HBP and was subsequently developed by transferring cells to a well in a 24 well plate and cultured in RPMI complete media. Media were changed three times per week. Cells were monitored daily and when cells seemed to have healthy growth, they were transferred to flasks in 10 mL of media and allowed to grow for approximately 2 w before monoclonal antibody was harvested. Hybridomas were monitored periodically for secretion and cloned approximately once every 6 to 8 w to remove non-secreting cells.

Determining Production Of Antibody

Enzyme-Linked Immunosorbent Assay. Enzyme-linked immunosorbent assay plates (Falcon, Fisher Scientific, Pittsburgh, Pa.) were coated with 50 μl of HBP (100 μg/mL) by incubating overnight at 4° C. Wells were washed twice with PBS with 0.05% TWEEN (polyoxyethlyenesorbitan, Sigma Chemical Co. St Louis, Mo.), then open sites were blocked with 1% nonfat dry milk in PBS for 30 min. Mouse serum (1:1,000) or cloned cell supernatant (100 μL) was added and incubated at 37° C. for 1 h, then washed twice with PBS-TWEEN. Goat anti-mouse second antibody (1:500; Tago, Burlingame, Calif.) conjugated to horseradish peroxidase was added and incubated for 1 h at 37° C. Wells were washed twice with PBS-TWEEN, then 50 μL of substrate (ABTS Substrate system, Kirkgaard and Perry, Gaithersburg, Md.) was added; the color developed in positive samples in minutes. The absorbance for each well was determined with an ELISA reader at 490 nm (DYNATECH 700, Chantilly, Va.).

Gel Electrophoresis and Western Blots. The HBP were identified using gel electrophoresis (SDS-PAGE) according to the method of Laemmli (1970) and Western blots as described by Deutscher (1990). Isolated HBP in PBS were vortexed vigorously, and added to sample buffer (1:1, 10% glycerol 2% SDS, 0.001% bromophenol blue in 62.5 mM TRIS), then tubes were placed in boiling water for 5 min. Samples (50 μg of HBP per lane) were pipetted onto a SDS/5% polyacrylamide stacking gel. Fifteen microliters of pre-stained molecular weight markers were applied to one lane per gel (Bio-Rad Laboratories, Hercules, Calif.). Samples were size-fractionated with denaturing SDS 12% polyacrylamide gel electrophoresis. Gels were run in duplicate and one gel was stained with Commassie brilliant blue G stain (Sigma Chemical) to visualize proteins.

Proteins on the second gel were transferred electrophoretically to IMMOBILON-PVDF membranes (Millipore Corporation, Bedford, Ma.). Membranes were blocked overnight at 4° C. or for 2 h at room temperature in phosphate buffered saline plus 3% (vol/vol) TWEEN-20 and 5% (wt/vol) bovine serum albumin (PBST-5% BSA). Membranes were rinsed five times in PBST-1% BSA and then incubated with mouse serum (1:1,000) or cloned cell supernatant (1 mL/lane). After an overnight incubation at 4° C., blots were washed five times in PBST-1% BSA. Blots were then incubated for 2 h at room temperature with a 1:3,000 dilution of second antibody, goat anti-mouse IgG conjugated to horseradish peroxidase (TAGO). Immobilized specific antigens were then detected using IMMUNOSELECT 4-chloro-1-naphthol (4CN, GIBCO BRL, Life Technologies, Gaithersburg, Md.). Other detection systems for Western Blots using alkaline phosphatase-conjugated secondary antibody with SIGMA FAST RED TR/NAPHTHOL AS-MX substrate (Sigma Chemical) or goat antimouse IgG conjugated to horseradish peroxidase secondary antibody (TAGO) with enhanced chemical luminescence (ECL, Amersham, Northbrook, Ill.) were also used according to the manufacturers directions in these studies.

Determining Proteins That Bind Heparin And Monoclonal Antibody. Sperm membrane and seminal fluid proteins that bind heparin and M1-coated affinity beads were compared. Heparin beads were prepared as described previously, and M1 affinity beads were prepared by binding M1 to AFFI PREP HZ HYDRAZIDE support (BioRad).

Briefly, seminal fluid (2 mL of semen) was removed from sperm by centrifugation at 1,400× g for 6 min, then sperm were washed three times and resuspended in 2 mL of isolation buffer (40 mM T, 250 mM sucrose, 2 mM ethylene diamine tetraacetic acid (EDTA), 5 mM benzamidine, 1 $\mu$M phenylmethylsulfonyl fluoride, 1 $\mu$M pepstatin A and 0.01% sodium azide, pH 7.35). Cells were disrupted by nitrogen cavitation in a PARR BOMB (Parr Instrument, Moline, Ill.) for 10 min at 600 psi (Noland et al, 1983). Suspensions of cavitated cells were microcentrifuged at 16,000× g for 20 min. Supernatants containing plasma membrane proteins (200 $\mu$L) or seminal fluid (200 $\mu$L) were added to 200 $\mu$L of heparin or M1 affinity beads, incubated for 10 min at 4° C., then washed three times with PBS with 0.05% TWEEN. Beads were suspended in 100 $\mu$L of buffer and 100 $\mu$L of sample buffer was added. Samples were boiled for 5 min and 40 $\mu$L per lane were applied to (SDS) 12%—polyacrylamide gels; Western blots using M1 were then performed as described previously.

STUDY 1: Determining Presence Of Heparin-Binding Protein With Monoclonal Antibody Using Enzyme-Linked Immunosorbent. Assay Of Sperm Membranes And Seminal Fluid From Bulls Semen Collection. A programmable electroejaculator (Electrojac, Chicago, Ill.) was used to collect semen samples from 53 Santa Gertrudis bulls at a commercial ranch (King Ranch, Kingsville, Tex.). Semen collection is part of the routine breeding soundness exams (BSE, Chenoweth et al, 1992) performed before spring breeding. Bulls were 3 to 7 yr of age. Sperm samples were examined visually for motility using a phase contrast microscope. One hundred sperm from an ejaculate were examined and visually identified as having normal or abnormal structure using a morphology stain (Society for Theriogenology, Hastings, Nebr.) and a light microscope (1000× magnification). Sperm were further characterized as having primary (head) or secondary (tail) abnormalities. In addition, scrotal circumference for each bull was measured. Semen was stored in ice until frozen (−20° C.), then shipped with dry ice to the University of Arizona (Tucson, Ariz.) and stored at −20° C. until samples were analyzed for HBP. Freezing of semen samples within 4 h of collection. Bulls with less than 70% normal sperm were removed from study and not used for breeding.

Seminal Fluid Proteins. Proteins were isolated from seminal fluid as described by Nass et al, (1990). Briefly, thawed semen (2 mL) samples were centrifuged at 1,200× g for 15 min at 4° C. Supernatant was applied to a PD-10 SEPHADEX G-25M column (BioRad) and washed with 0.05 M ammonium bicarbonate (pH 8.5) to remove excess salt. Samples were lyophilized and stored at −20° C. until they were analyzed for HBP with ELISA. The sperm pellets were frozen (−70° C.) until proteins were isolated.

Sperm Membrane Proteins. Sperm pellets were thawed and washed three times with 1 mL of TC buffer at 4° C. Washed pellets were resuspended in 1 mL of TC buffer containing 0.1% (vol/vol) TRITON X-100 and incubated for 1 h at 4° C. Then, 3 mL of 0.1% TC buffer was added and the cells were centrifuged at 50,000× g for 30 min to remove the cellular debris (Nass et al, 1990). Supernatants containing sperm membrane proteins were lyophilized and stored at −20° C. until they were analyzed for HBP with ELISA.

Testing For Presence Of Heparin-Binding Proteins. Seminal fluid and sperm membrane proteins were solubilized in 500 and 200 $\mu$L of deionized distilled water, respectively. Seminal fluid or sperm membrane proteins were added (100 $\mu$L) to an ELISA plate in duplicate. Monoclonal antibody (M1, 100 $\mu$L) was added to each well and the ELISA were performed as previously described.

Grouping of Bulls According to Heparin-Binding Protein Profiles. Trials were conducted at a large commercial ranch (King Ranch, Kingsville, Tex.), and it was not possible to test fertility of individual bulls. Instead, bulls were identified and grouped according to the presence or absence of HBP in sperm membranes and seminal fluid as determined by ELISA.

Pasture Assignments. Groups were assigned to a pasture based on the number of bulls needed to meet the pasture requirements. Bulls were pastured at a ratio of 1 bull:25 cows. To eliminate bias of selection of pastures, actual HBP characteristics for each group were coded and not identified to King Ranch personnel until completion of the trials. Bulls were identified by ear tags, matched to their coded HBP group and the appropriate pasture assignment was spray painted on their backs. Bulls were transported to each pasture. All cows used in these studies were Santa Gertrudis and had calved in the spring before the trial. Pastures contained native grasses, and cattle were supplemented with Mintrate mineral blocks (MoorMan's Mfg., Quincy, Ill.).

Determination of Fertility. Bulls were pastured on approximately May 1 with cows for 60 d, then they were removed. After an additional 60 d, cows were checked for pregnancy by palpation per rectum. Because the pastures were large, not all cows were recovered from each pasture at the time of palpation. Fertility for each group of bulls was computed as the number of cows determined pregnant divided by the total number of cows palpated.

Study 2: Determining Specific Heparin-Binding Proteins In Sperm Membranes With Western Blots Semen Collection. Semen samples were collected from 62 (3- to 7-yr. old) and 30 (2-yr) Santa Gertrudis bulls by electroejaculation and processed, as described previously.

Sperm Membrane Proteins. Semen samples were thawed and 200 $\mu$L of each sample were washed once with 1 mL of PBS at 4° C. in a 5415 C EPPENDORF microcentrifuge (Brinkmann Instruments, Inc., Westbury, N.Y.) at 6,000× g for 5 min. Sperm proteins were applied to SDS-PAGE gels as previously described.

Samples (30 $\mu$l of sperm pellets resuspended in 0.1 mL PBS buffer and 0.1 mL of sample buffer) were applied to each lane of a 12% gel Western blots with indirect second antibody and Sigma Fast Red detection of HBP were used, as described previously.

Grouping Of Bulls According To Heparin-Binding Protein Profiles. The presence of three proteins in sperm samples approximately 30, 24 and 21.5 kDa were analyzed. Bulls were identified and grouped according to the number of HBP bands recognized in sperm by the monoclonal antibody.

Pasture Assignments And Determination of Fertility. Groups of bulls were assigned to a pasture based on the number of bulls needed to meet the pasture requirements and cows were checked for pregnancy as described previously.

Statistical Analyses

Chi-square two by two contingency tests were used to determine differences in pregnancy outcomes for cows bred to bulls with different patterns of HBP assayed with ELISA or Western blots.

Results

Recognition of Proteins by Monoclonal Antibody

Sperm membranes and seminal fluid yielded similar protein bands on SDS-PAGE (FIG. 1a), even though relative darkness of staining indicated less proteins were applied from sperm membrane (lanes 1, 2 and 6) compared to seminal fluid (lanes 10, 12, 13). Heparin and M1 affinity purification of samples before they were separated with PAGE decreased the amounts of protein in sperm membrane (lanes 5 and 4, respectively) and seminal fluid (lanes 9 sand 8, respectively).

Figure 1A:
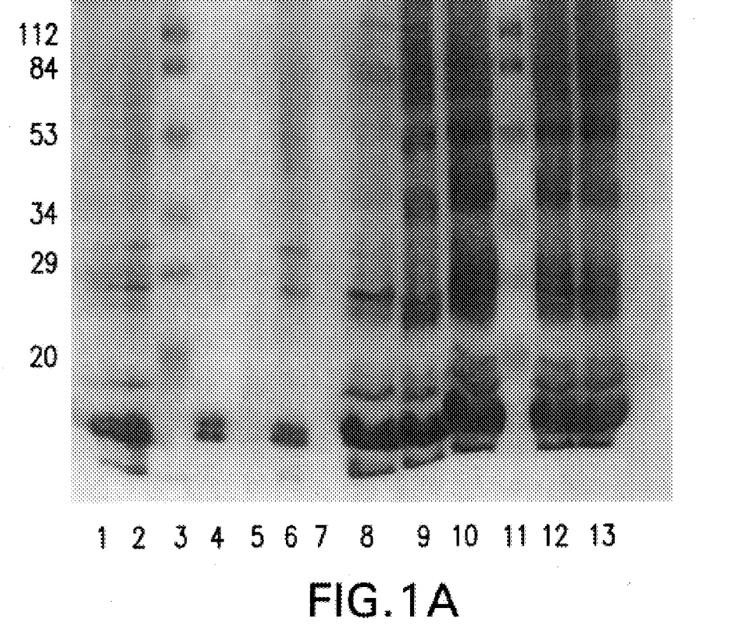
FIG. 1a. A Commassie blue stained SDS-PAGE of sperm membranes (Lanes 1, 2 and 6) and seminal fluid (Lane 10, 12 and 13) from a beef bull. Heparin (lane 5 and 9) and M1 (lane 4 and 8) affinity purified proteins from sperm membranes and seminal fluid, respectively, indicated that proteins with affinity to M1 and heparin were similar. Molecular masses of standards (lanes 3 and 11) and an 29 kDa marker (lane 7) were indicated on the left.
Figure 1B:
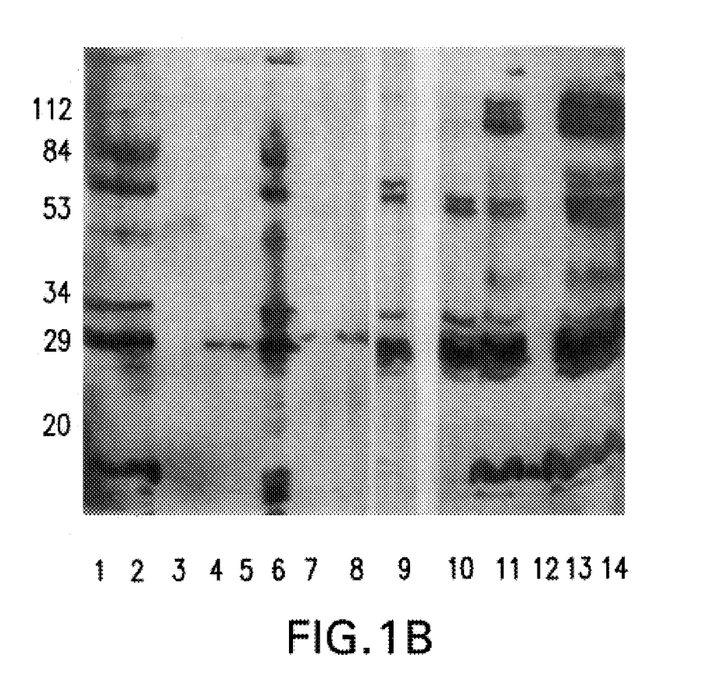
FIG. 1b. Autoradiograph of Western blot hybridization using monoclonal antibody (M1) to sperm membranes (Lanes 1, 2 and 6) and seminal fluid (Lane 11, 13 and 14) from a beef bull. Proteins at 84, 49–66, 30, 24, 21.5 and 12 kDa were recognized by M1 in sperm and additional bands at 99–112 and 35 in fluid samples. Heparin (lane 5 and 10) and M1 (lane 4 and 9) affinity purified proteins from sperm membranes and seminal fluid, respectively, indicated that similar proteins bind to heparin and M1. Molecular masses of standards (lanes 3 and 12) and a 29 kDa marker recognized by enhanced chemical luminescence (lanes 7 and 8) were indicated on the left. Radiograph was developed with enhanced chemical luminescence.

Western blots indicated that the monoclonal antibody (M1) recognized multiple bands at approximately 112, 106, 99, 66, 59, 51, 49, 35, 30, 24, 21 and 12 kDa in seminal fluid (FIG. 1b, lanes 11, 13, and 14) and at 84, 66, 49 to 51, 41 to 43, 30, 24, 21 and 12 kDa in sperm membranes (FIG. 1b, lanes 1, 2 and 6). Heparin affinity purification of proteins was performed to determine which HBP were recognized by M1. Heparin purification of seminal fluid proteins before application to PAGE/Western blots resulted in detection of proteins at 51, 49, 30, 24 and 21 kDa by M1 (FIG. 1b, lane 10). The other protein bands present in seminal fluid (lanes 11, 13, 14) at 99 to 112, 59 to 66, 35 and 12 kDa seemed not to bind heparin (lane 10). Affinity purification of sperm proteins required PARR BOMB isolation of membrane proteins, therefore, concentrations of proteins were greatly reduced (FIG. 1a: lanes 4 and 5). The 24-kDa heparin binding protein in sperm membranes was recognized by M1 (FIG. 1b, lane 5).

Heparin compared to M1 affinity, purification before PAGE resulted in detection of similar proteins in sperm membranes (FIG. 1b: lane 5 vs lane 4, respectively) and seminal fluid (FIG. 1b: lane 10 vs lane 9, respectively). Seminal fluid protein bands at 99 to 112, 59 to 66, 35 and 12 kDa (lane 11) seem not to recognize M1 attached to the affinity matrix (lane 9), and they were not detected.

Figure 2A:
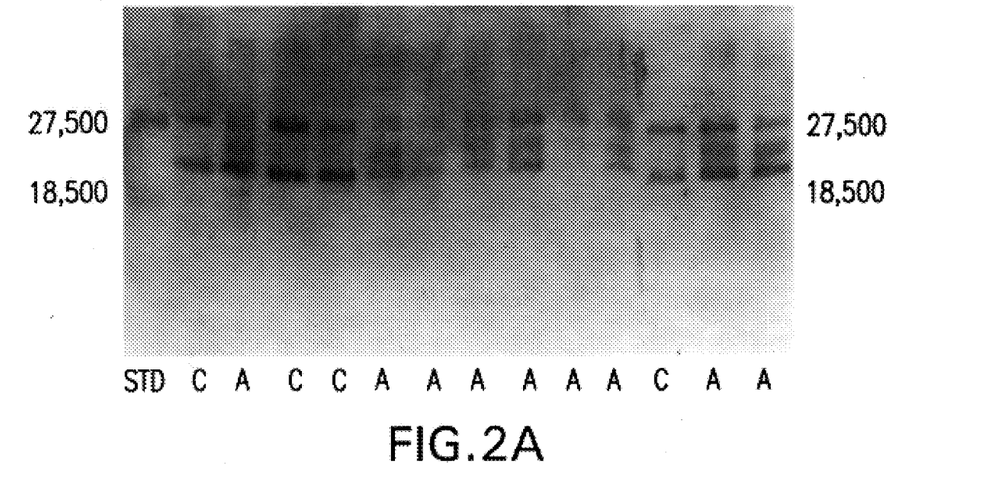
Figure 2B:
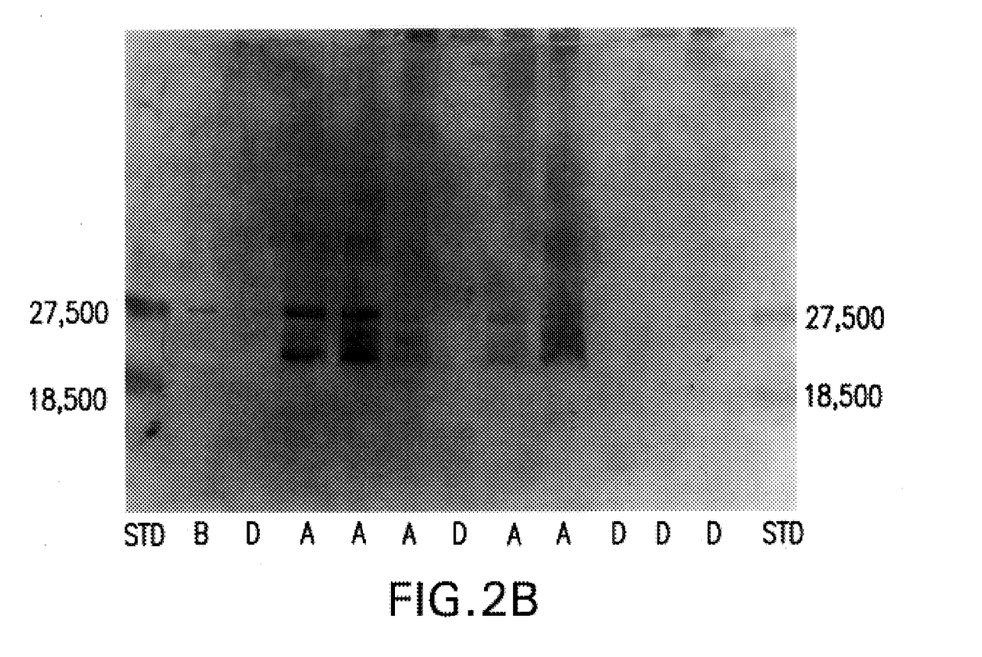

In conclusion, M1 recognized multiple heparin binding proteins (51, 49, 30, 24 and 21 kDa) and a group of proteins (99 to 112, 59 to 66, 35 and 12 kDa) in fluid that did not seem to bind heparin or M1 attached to affinity matrix. Detection of proteins with FAST RED and ECL detection systems for Western blots did not differ. 10 Western blots stained with FAST RED were used in Study 2 and are shown in FIG. 2.

Study 1: Detecting Heparin-Binding Proteins Using an Enzyme-Linked Immunosorbent Assay Presence of total proteins recognized by M1 in sperm or seminal fluid was determined using ELISA. Even though M1 recognized multiple proteins, the term HBP was used to indicate positive ELISA results. Semen from 63 Santa Gertrudis bulls was tested and resulted in four groupings. Twelve bulls (19%) had HBP on sperm but with undetectable HBP in fluid (Group 1). Group 2 had bulls (25%, n=16) with HBP detectable in sperm and in fluid. Bulls (40%, n=25) with undetectable HBP in fluid and sperm were in assigned to Group 3, and bulls (16%, n=10) with HBP in fluid but not in sperm were assigned to Group 4. Pasture assignments resulted in 8, 10, 18 and 8 bulls from Groups 1, 2, 3 and 4 with 207, 257, 441 and 209 Santa Gertrudis cows in each pasture, respectively (Table 1). Concentrations of sperm and BSE scores did not differ among groups (p>0.05 data not shown).

TABLE 1

Pasture assignments including number of Santa Gertrudis bulls grouped according to presence or absence of heparin-binding proteins (HBP) in seminal fluid and sperm membranes as determined with ELISA, number of Santa Gertrudis cows and pasture size (ha) for each group

| | Sperm membrane HBP | |
|---|---|---|
| Seminal fluid HBP | Present | Absent |
| Absent | Group 1<br>8 bulls<br>207 cows<br>2,274 ha | Group 3<br>18 bulls<br>441 cows<br>2,743 ha |
| Present | Group 2<br>10 bulls<br>257 cows<br>2,274 ha | Group 4<br>8 bulls<br>209 cows<br>1,489 ha |

Bulls that had positive identification of HBP by M1 in sperm membranes were more (p<0.01) fertile. Pregnancy rates were 89.1% and 89.2% for cows palpated in Groups 1 and 2, respectively, and 78.1% and 79.1% for cows palpated in Groups 3 and 4, respectively (Table 2).

TABLE 2

Fertility (percentage of Santa Gertrudis cows pregnant of total number of palpated cows) and number of pregnant/total palpated cows (x) among Santa Gertrudis bulls grouped according to presence or absence of heparin binding proteins (HBP) in seminal fluid and sperm membranes as determined with ELISA

| | Sperm membrane HBP | |
|---|---|---|
| Seminal fluid HBP | Present | Absent |
| Absent | Group 1<br>89.1%$^a$<br>(147/165) | Group 3<br>78.1%<br>(200/256) |
| Present | Group 2<br>89.2%$^a$<br>(174/195)<br>2,274 ha | Group 4<br>79.1%<br>(140/177)<br>1,489 ha |

$^a$p < .01 compared with other values in the same row.

Presence of HBP in seminal fluid was not indicative of fertility. Therefore, bulls with detectable HBP on sperm membranes were 11 percentage point more fertile than bulls with undetectable HBP on sperm membranes as determined by ELISA (p<0.01).

Study 2: Detecting Heparin-Binding Proteins with Western Blots

Presence of three HBP (30, 24 and 21.5 kDa) in sperm membranes were recognized by M1 using Western blots. Four band patterns were detected and classified as Groups A to D, (FIG. 2). Santa Gertrudis bulls were grouped according to the pattern of three HBP in sperm (Table 3).

TABLE 3

Number and percentage of total older (3 to 7 yr) and younger (2 yr) bulls in each heparin-binding protein (HBP) group as determined with Western blots

| | HBP Bands, | Mature Bulls | | Young Bulls | |
|---|---|---|---|---|---|
| Group | kDa | Number | % | Number | % |
| A | 30, 24, 21.5 | 33 | 67.3 | 20 | 66.7 |
| B | 30 | 2 | 4.1 | 0 | 0 |
| C | 30 and 21.5 | 6 | 12.2 | 0 | 0 |
| D | No bands | 8 | 16.3 | 10 | 33.3 |
| Total | | 49 | | 30 | |

Of the 49 older bulls (3 yr or older) in which HBP was determined, 67.3% had three HBP bands (30, 24 and 21.5 kDa: Group A) and 4.1% had a single 30 kDa HBP band (Group B). Some bulls (12.2%) had 21.5 and 30 kDa HBP, with the 24 kDa HBP absent (Group C). One group of bulls (16.3%) did not have any of the three HBP bands present in sperm (Group D). There were 30 young bulls (2 yr) tested for HBP. Twenty of the younger bulls were classified as Group A (66.7%) and 10 bulls (33.3%) had no visible HBP bands (Group D). Concentrations of sperm and breeding soundness scores did not differ among Groups (p >0.05 data not shown).

There were 41 older and 14 younger bulls grouped, pastured and bred to 1,354 Santa Gertrudis cows (Table 4).

TABLE 4

Fertility (percentage of Santa Gertrudis cows pregnant of total number of palpated cows) for each pasture containing Santa Gertrudis bulls grouped according to presence of heparin binding protein (HBP) in sperm as determined by Western Blots

| Pasture Number | Group[a] | Number of Bulls Pastured | Number of Cows Pastured | Number of Cows Palpated | Fertility, % |
|---|---|---|---|---|---|
| 1 | A | 8 | 191 | 166 | 84.3 |
| 2 | A | 9 | 226 | 199 | 73.4 |
| 3 | A | 6 | 138[e] | 127 | 89.9 |
| 4 | A | 11[b] | 270 | 218 | 84.9 |
| 5 | A | 5[c] | 132[e] | 119 | 74.8 |
| Average | A | | | | 81.3 |
| 6 | B | 2 | 53 | 46 | 86.9 |
| 7 | C | 6 | 155 | 124 | 61.3[f] |
| 8 | D | 7[d] | 189 | 186 | 41.9[f] |
| 9 | E | 11 | 265 | 213 | 75.1[g] |

[a]Group A-HBP bands 30, 24, 21.5 kDa; Group B-HBP bands 30 kDa; Group C-HBP bands 30 and 21.5 kDa; Group D-no HBP bands; Group E-bulls not tested for HBP.
[b]bulls were 2 years old.
[c]Three bulls 2 years old, and 2 bulls were 2 to 7 years old.
[d]pasture contained 6 bulls with no bands and one A (30, 24, 21.5 kDa) bull.
[e]Cows were 2 years old and had calved once.
[f]Values differ from Group A, p < 0.001.
[g]Values differ from Group A, p < 0.05.

Not all bulls tested for HBP were used in the study. the HBP was not determined in one group of bulls (n=11, Group E), which were randomly selected from bulls that had passed the BSE. This group served as a control and was representative of bulls pastured at the ranch.

Groups of bulls with different HBP bands present in sperm membranes varied in fertility (Table 4). Groups A and B bulls had the greatest fertility, ranging from 74.4 to 89.9% (with an average of 81.3%) of the palpated cows pregnant. Group C bulls had a reduced fertility of 61.3%. Bulls without any detectable HBP bands present in sperm (Group D) had a fertility value of 41.9%. The bulls that had not been tested for HBP (Group E) had fertility of 75.1%. Group A and B bulls were more (p<0.01) fertile than all other groups.

Five Santa Gertrudis and five Santa Cruz (½ Santa Gertrudis, ¼ Red Angus and ¼ Gelbvieh) bulls with Group A patterns were selected and used in six small research pastures containing one or two bulls (Table 5).

TABLE 5

Fertility (percentage of Santa Gertrudis cows pregnant of total number of palpated cows) for each pasture containing one or two Santa Gertrudis and Santa Cruz bulls grouped according to presence of HBP in sperm as determined by Western Blots

| Pasture Number | HBP Group[a] | Number of Bulls Pastured | Cows Palpated | Pregnant Cows (%) |
|---|---|---|---|---|
| 10 | A/D | 2[b] | 43 | 95.0 |
| 11 | A | 1[b] | 23 | 100.0 |
| 12 | A | 2[b] | 51[d] | 80.3 |
| 13 | A | 2[c] | 44[e] | 88.6 |
| 14 | A | 1[c] | 33 | 96.9 |
| 15 | A | 2[c] | 57 | 89.9 |

[a]Group A-HBP bands 30, 24, 21.5 kDa; Group D-no HBP bands;
[b]Santa Gertrudis bulls bred to Santa Gertrudis cows.
[c]Santa Cruz bulls bred to Santa Cruz cows.
[d]Cows were 8 years old or older, the average age was between 10 and 14 years.
[e]Cows were visually very thin at the start of the breeding season.

Fertility ranged from 80 to 100%; average fertility was 92.7% of the palpated cows pregnant.

Conclusion

Identifying the presence of a 21.5-, 24-, and 30-kDa heparin-binding proteins in sperm membranes with a monoclonal antibody allowed us to separate bulls into groups that differed in fertility by 40 percentage points. Thus, fertility potential of a bull can be predicted by heparin-binding protein content of sperm membranes.

Literature Cited

Ax and Lenz 1987. J. Dairy Sci. 70:1477.
Ax et al, 1985. J. Dairy Sci. 68:387.
Bellin et al, 1994. J. Anim. Sci. 72:2441.
Chandonnet et al, Mol.Reprod. and Dev. 26:313.
Chenoweth et al, 1992. A new breed soundness evaluation form. Society for Theriogenology, Proc: for Annu. Mtg, August 14–15, San Antonio, Tex.
Cowan et al, 1986. J. Cell Biol. 103:1289.
Desnoyer and Manjunath. 1992. J. Biol. Chem. 267:10149.
Deutscher, 1990. Guide to Protein Purification, Methods in Enzymology, Dept of Biochem. University of Connecticut Health Center, Farmington, Conn. Academic Press, Inc. Harcourt, Brace, Jovanovich, Publishers, San Diego, Calif. 182:425.
Enriquez et al, 1991. Hybridoma 10:745.
Handrow et al, 1982. Biochem. Biophys. Res. Commun. 107:1326.
Henault et al, 1995. Biol. Reprod. 52:390.
Kohler and Milstein. 1975. Nature 256:495.
Laemmli, 1970. Nature 227:680.
Lee et al, 1985. Gamate Res. 12:345.
Lenz et al, 1988. J. Dairy Sci. 71:1073.
Lenz et al, 1983. Biol. Reprod. 28:683.

Manjunath, and Sairam. 1987. Biochem. J. 241:685.
Marks, and Ax. 1985. J. Dairy Sci. 68:2078.
Miller et al, 1990. 42:899.
Myles and Primakoff. 1984. J. Cell Biol. 99:1634.
Nass et al, 1990. Mol. Reprod. and Dev. 25:237
Noland et al, 1983. Biol. Reprod. 29:987.
Seidah et al, 1987. Biochem. J. 243:195.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by: Letters Patent of the United States is:

1. A method for determining the fertility of a bull or other mammal, comprising:
   (i) obtaining a sample of semen from said bull or other mammal; and
   (ii) measuring the amount of heparin binding proteins (HPBs) of molecular weight 30,000, 24,000 and 21,500 in said sample of semen, by contacting monoclonal antibodies which specifically bind to said HPBs to said sample and measuring the amount of said HPBs bound to said antibodies in said sample.

2. The method of claim 1, wherein said measuring is performed by enzyme linked immunosorbent assay.

3. The method of claim 1, wherein said measuring is performed by Western blots.

4. The method of claim 1, wherein said monoclonal antibody is produced by hybridoma ATCC accession No. HB 11916.

5. The method of claim 1, wherein said monoclonal antibody is produced by hybridoma ATCC accession No. HB 11928.

6. A method for determining the fertility of a bull or other mammal, comprising:
   (i) obtaining a sample of sperm-containing semen from a bull or other mammal;
   (ii) isolating sperm from said semen sample;
   (iii) lysing said isolated sperm to release seminal heparin binding proteins; and
   (iv) measuring the amount of said seminal binding proteins of molecular weight 30,000, 24,000 and 21,500, wherein moleccular weight is determined by polyacylamide gel electrophoresis.

* * * * *